(12) United States Patent
Luo et al.

(10) Patent No.: US 9,007,594 B1
(45) Date of Patent: Apr. 14, 2015

(54) GAS DETECTION SYSTEM USING FIBER LASER WITH ACTIVE FEEDBACK COMPENSATION BY REFERENCE CAVITY

(71) Applicant: Beijing Information Science & Technology University, Beijing (CN)

(72) Inventors: Fei Luo, Winchester, MA (US); Lianqing Zhu, Beijing (CN); Mingli Dong, Beijing (CN); Wei He, Beijing (CN); Yinmin Zhang, Beijing (CN)

(73) Assignee: Beijing Information Science & Technology University, Beijing (CN)

( * ) Notice: Subject to any disclaimer, the term of this patent is extended or adjusted under 35 U.S.C. 154(b) by 0 days.

(21) Appl. No.: 14/503,829

(22) Filed: Oct. 1, 2014

(30) Foreign Application Priority Data

Oct. 14, 2013 (CN) .................. 2013 1 04788372

(51) Int. Cl.
*G01N 21/00* (2006.01)
*G01N 21/61* (2006.01)

(52) U.S. Cl.
CPC ...... *G01N 21/61* (2013.01); *G01N 2201/06113* (2013.01); *G01N 2201/0635* (2013.01)

(58) Field of Classification Search
None
See application file for complete search history.

(56) References Cited

FOREIGN PATENT DOCUMENTS

| CN | 1912585 A | 2/2007 |
|---|---|---|
| DK | 2137512 T3 | 4/2011 |
| JP | 2006337068 A | 12/2006 |

OTHER PUBLICATIONS

Liu, Chun Yu et al., Accuracy control of coupling ratio, Optical Technique, 2004, vol. 30 No. 6, pp. 743-744.
Patent Search & Consulting Center of State Intellectual Property Office, "Search Report", Nov. 20, 2013, pp. 1-6.

*Primary Examiner* — Kara E Geisel
*Assistant Examiner* — Amanda Merlino
(74) *Attorney, Agent, or Firm* — Tim Tingkang Xia, Esq.; Morris, Manning & Martin, LLP

(57) ABSTRACT

The present invention provides a fiber laser gas detection system using active feedback compensation by a reference cavity, said system comprising: an optical fiber laser consists of a laser diode pump source, a wavelength division multiplexer, an active optical fiber and a fiber Bragg grating connected successively; an optical isolator coupled with said wavelength division multiplexer for blocking a reverse light transmission in said active fiber; a coupler connected with said optical isolator for dividing the laser light after being isolated by the optical isolator into a reference beam, a detecting beam and an intensity measuring beam according a certain ration power. The gas detection system according to the present invention can take advantages of the unique superiority of compact structure and narrow linewidth of the laser output of the fiber laser, and achieve a gas detection method with high sensitive and high precision by feedback controlling.

10 Claims, 3 Drawing Sheets

GAS DETECTION SYSTEM USING FIBER LASER WITH ACTIVE FEEDBACK COMPENSATION BY REFERENCE CAVITY

CROSS-REFERENCE TO RELATED APPLICATIONS

This non-provisional application claims priority under 35 U.S.C. §119(a) on Patent Application No. 2013104788372 filed in P.R. China on Oct. 14, 2013, the entire contents of which are hereby incorporated by reference.

TECHNICAL FIELD

The present invention relates to fiber laser, particularly relates to a gas detection system and method for the gas concentration measurement implemented by the distributed feedback fiber laser, which uses a reference cavity for active feedback compensation.

BACKGROUND OF THE INVENTION

Laser plays an important role in modern spectroscopy, due to its high monochromaticity (narrow spectral line), high brightness, high directivity and other unique advantages. A new laser spectroscopy develops, with a high application value in various research fields such as modern agriculture and environmental science, biology and medical science, physics, chemistry and materials science and astrophysics, and in industrial process monitoring.

Laser was used for gas detection has an important application value in environmental detection and analysis, as well as a variety of industrial process control, etc. Many types of gas has its characteristic spectral lines, so certain gases can be detected by using the characteristics of the laser of narrow linewidth. One of common gas detection methods by laser is to adjust or set the wavelength emitted from the laser to be consistent with the characteristic absorption spectrum line of the gas to be detected, to transmit the laser through the gas chamber, and thus to determine the concentration of the gas by measuring the attenuation of the laser after transmitting through the gas cavity. This detecting method is simple in both the principle and the structure. However, generally the light source has a wide spectral linewidth, and some of the gases have very narrow absorption lines, so the optical power does not change obviously when passing through the gas chamber, which lowers and limits measuring sensitivity. Especially, it is more difficult for detecting tiny gas concentration.

The conventional differential absorption method is based on two beams in a common optical path passing through the same gas cavity to be detected. The output beam wavelength $\lambda 1$ of one beam is consistent with the characteristics absorption lines of the gas to be detected. And the output beam wavelength $\lambda 2$ of the adjacent beam is selected near the absorption lines of the gas to be detected, but not exactly the same with its absorption lines, to be used as a reference light in order to eliminate the instability of light intensity in the light path. However, this detection method does not eliminate the detection error caused by the instability of the wavelength of light $\lambda 1$, which can not be ignored in the practical detection. Therefore, in the prior art, the differential absorption method is improved. Commonly, the laser current and temperature is stabilized to realize a stable wavelength outputted from the laser $\lambda 1$. However such a regulation method is passive, do not strictly eliminate fluctuations of the laser $\lambda 1$, thus such an improvement do not obtain good effects.

Fiber laser is a new type laser developed rapidly in recent years. Fiber laser uses a fiber optic waveguide as a gain medium and an optical fiber grating as a feedback mirror to form an integrated optical fiber resonator, thus providing advantages such as compact structure, narrow laser linewidth, high beam quality, and a laser system with high reliability, good stability and maintenance-free, which makes a huge impact on the laser industry. Development of modern spectral composition detection and analysis system based on fiber laser will not only has great significance to the development of laser spectroscopy, but also make the fiber laser spectral analysis system more portable to be used expediently.

Therefore, it is a technical problem to be solved in this field as how to apply the fiber laser in the field of gas concentration detection taking various advantages of the fiber laser, such as its compact structure, narrow linewidth of the laser output. There is a need for a gas concentration measurement method and system which not only taking advantages of fiber laser but also obtaining high sensitivity and high precision of gas detection.

SUMMARY OF THE INVENTION

The present invention provides a fiber laser gas detection system using active feedback compensation by a reference cavity, said system comprising: an optical fiber laser consists of a laser diode pump source, a wavelength division multiplexer, an active optical fiber and a fiber Bragg grating connected successively; an optical isolator coupled with said wavelength division multiplexer for blocking a reverse light transmission in said active fiber; a coupler connected with said optical isolator for dividing the laser light after being isolated by the optical isolator into a reference beam, a detecting beam and an intensity measuring beam according a certain ratio of power; a reference gas chamber, which is introduced with a reference gas of the same composition as that of the gas to be detected and of a known concentration, and receives the reference beam allocated from the coupler and makes it pass through the reference gas; a detecting gas chamber, which is introduced with the gas to be detected, and receives the detecting beam allocated from the coupler and makes it pass through the gas to be detected; a first photodetector connected to said reference gas chamber for receiving the reference beam passing through the reference gas chamber to generate a first light intensity signal; a second photodetector connected to said detecting gas chamber for receiving the detecting light beam passing through the detecting gas chamber to generate a second light intensity signal; a third photodetector connected to said coupler for receiving said intensity measuring beam to generate a third light intensity signal; a feedback control unit for receiving and comparing said first, second and third light intensity signals, and converting the comparison result into a feedback signal to adjust said pump source and said fiber Bragg grating.

Preferably, the power ratio of the reference beam, the detecting beam and the intensity measuring beam is 1:1:1.

Preferably, the feedback control method of the feedback control unit comprising the steps of: a) determining whether the output of the fiber laser is stable, if it is not stable, outputting a first feedback control signal to adjust the power output of the pump source until it is stable; b) determining whether the wavelength range of the signal mode outputted from the fiber laser covers the characteristics spectral lines of the gas to be detected, if it does not cover, then outputting a second feedback control signal to adjust the reflectivity of fiber Bragg grating until it covers; c) comparing the signal intensities of the first and second light intensity signals to obtain the result of comparing the concentrations of the gas to be detected and the reference gas.

Preferably, said step b) is achieved by comparing if the intensity value of said first or second light intensity signal is substantially smaller than that of the third light intensity signal to determine whether it covers.

Preferably, it further comprises a laser control unit attached to the fiber Bragg grating, and the deformation of the laser control unit is controlled by said second feedback control signal so as to change the laser resonator cavity length.

Preferably, the laser control unit is made of PZT piezoelectric ceramic or TE temperature control unit.

Preferably, the gas detection system is a wavelength division multiplexed device of 1×2.

Preferably, it further comprises a spherical lens for respectively coupling the reference beam and the detecting beam into the reference gas chamber and the detecting gas chamber so as to emit therefrom.

Preferably, the active fiber is an ytterbium-doped fiber, or erbium-doped fiber or erbium ytterbium co-doped fiber.

Preferably, said detecting gas chamber comprises a gas inlet to introduce the gas to be detected before detection and a gas outlet to exhaust the gas.

The gas detection system according to the present invention can take advantages of the unique superiority of the compact structure and narrow linewidth of the laser output of the fiber laser, and achieve a gas detection method with high sensitive and high precision by feedback controlling. The method and system are not limited to apply to high sensitivity detection of gas content, but also easily apply to the detection with high sensitivity and material analysis of other materials.

It should be understood that the foregoing general description and the following detailed description are merely exemplary explanation, and shall not be construed as limiting the contents as claimed by the invention.

BRIEF DESCRIPTION OF DRAWINGS

Further objects, functions, and advantages of the present invention will be explained in details by embodiments of the present invention with reference to the accompanying drawings.

DETAILED DESCRIPTION OF THE INVENTION

Figure 1:
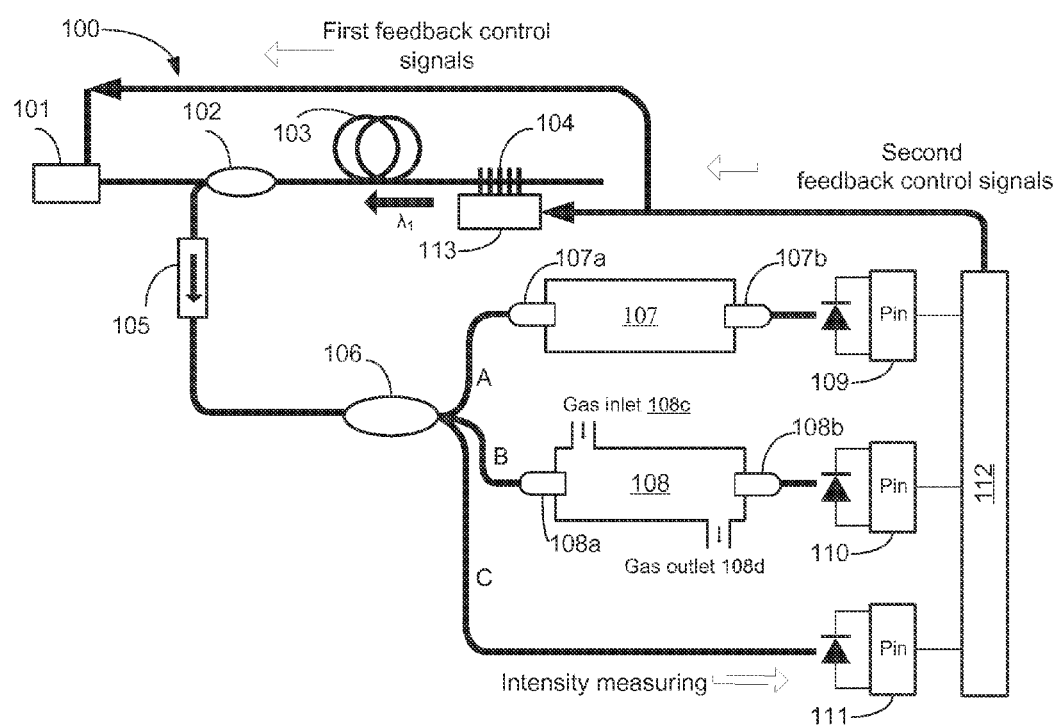
FIG. 1 schematically shows a gas detection system based on the distributed feedback fiber laser according to the present invention.

Hereinafter, embodiments of the present invention will be explained in details with reference to drawings. In the accompanying drawings, like reference numerals designate the same or similar parts, or the same or similar procedures.

With reference to the exemplary embodiments, the purpose and function of the present invention and method to achieve these purpose and function will be explained. However, the present invention is not limited to the disclosed exemplary embodiments, and can be implemented with different forms. The description in nature is merely to help those skilled in the art to comprehensively understand the specific details of the invention.

The present invention will be described in detail with reference to the schematic figures. For the purpose of explanation, when describing the invention in details, the sectional figures representing the device structure will be partial enlarged not in general proportion, and the schematic figures are only exemplary and not intended to limit the scope claimed by the invention. Moreover, it should comprise three space dimensions of length, width and depth in the actual production.

The present invention provides a gas detection system based on the distributed feedback (DFB) fiber laser, which is characterized in using a semiconductor laser as a pump source of the DFB fiber laser, emitting a laser of specific wavelength, coupling the laser into a coupler by the wavelength division multiplexer (WDM), dividing the input light into three beams by the coupler, projecting two of the three beams into the reference gas chamber and detecting gas chamber respectively for differential comparison, and projecting the third one for the DFB laser intensity detection. Transmission beams are detected by the photoelectric detectors, and the signals received are analyzed and processed to achieve feedback control of the DFB fiber laser. The system eliminates the interferences to measurement caused by the intensity fluctuation and the environmental interferences, so as to implement accurate measurement of the gas to be detected. The gas detection system according to the present invention is particularly suitable for threshold detection of tiny gas concentration in certain situation for gas safety alarm.

With full use of the unique advantages of the fiber laser such as the compact structure and emitting laser beam with several narrow linewidths, the present invention adopts the distributed feedback (DFB) semiconductor laser, which is a kind of single longitudinal mode semiconductor laser (Laser Diode) with excellent frequency selective characteristics. DFB LD light source can operate in a single longitudinal mode with the output laser having a narrow spectral linewidth which is up to tens of kilohertz, and can make the operating laser wavelength precisely aligning with the characteristic absorption peaks of the gas being measured by regulating the temperature or the drive current of the laser, to obtain high measurement precision.

Generally the spectral absorption detection satisfies Bill-Lambert's law:

$$I(\lambda)=I_0(\lambda)\exp[-\alpha(\lambda)CL] \quad (1)$$

Wherein, I is the intensity of the light transmitted through the medium to be detected, $I_0$ is the intensity of the light inputted into the medium to be detected, $\alpha$ is the molar absorption coefficient, C is the concentration of the medium to be detected, L is the length of the absorption path for the medium to be detected. Generally it is known that the incident light intensity is $I_0$, the absorption coefficient for the gas to be detected in its characteristic spectral lines is $\alpha$, the length of the gas sampling cavity for measuring the gas to be detected is L, the concentration of the gas C can measured by measuring the optical signal attenuation of the laser with the specific wavelength after it comes through the gas absorption chamber.

Generally, the light can be interfered by various factors in the light transmission path, such as the vibration, the unstable output beam wavelength of the laser, etc. All factors will seriously interfere with the actual measurement result. Considering the influence of these factors, the principle of spectral absorption detection can be revised to:

$$I(\lambda)=I_0(\lambda)K(\lambda)\exp[-\alpha(\lambda)CL+\beta(\lambda)] \quad (2)$$

Wherein, K (λ) is the fluctuation of the light source and the light transmission path, β (λ) is the measurement uncertainty caused by the laser spectrum fluctuation, thus the key problem in measuring the gas concentration by the conventional absorption method is how to effectively reduce the influence on measurement by K (λ) and β (λ).

FIG. 1 shows the gas detection system based on distributed feedback fiber laser according to the present invention. The gas detection system 100 according to the present invention includes the following components: a fiber laser consists of a laser diode pump source 101, a wavelength a division multiplexer 102, a active optical fiber 103 and a fiber Bragg grating 104 connected successively, a optical isolator 105 coupled with the wavelength division multiplexer 102, a optical isolator coupler 106 connected with the optical isolator 105. The optical isolator coupler 106 is connected with a reference gas chamber 107, a detecting gas chamber 108, and a third photoelectric detector 111 for detecting the light signal intensity, and the other ends of the reference gas chamber 107 and the detecting gas chamber 108 each respectively are connected with a first photoelectric detector 109 and a second photoelectric detector 110, which are used for detect respectively the light signal intensity after the light passes through each gas chamber. The output ends of the first photoelectric detector 109, the second photoelectric detector 110 and the third photoelectric detector 111 are connected to the feedback control unit 112, and the signals are controlled to be feedback adjusted and then inputted into the laser control unit 113 for laser feedback control.

The pump source 101 projects a pump light which is coupled into the active optical fiber 103 by the wavelength division multiplexer (WDM) 102, and the active optical fiber 103 combines with the fiber Bragg grating 104 direct written on the active optical fiber 103 to form a resonant cavity, which constitute the DFB fiber laser. Preferably, the wavelength division multiplexer 102 is 1×2 wavelength division multiplexer, allowing two lights of different wavelengths transmit in the same optical fiber.

The parameters of the fiber Bragg grating 104 can be adjusted to obtain a laser output with a specified wavelength. Laser requires an output in single longitudinal mode. The narrower the output linewidth is, the better the linewidth of the output of the laser is coincident with the absorption characteristic spectral lines of the gas, the higher the measuring precision of gas concentration is. The active optical fiber 103 can choose a shorter length (for example in cm orders of magnitude), preferably it is doped with rare earth elements and has a high doping concentration (such as erbium ytterbium codoping, peak absorption in 40+10 db/m @ 1535 nm), in order to reduce the threshold of the pump system. The fiber Bragg grating 104 has high reflectivity (the reflectance can be more than 90% for a specific wavelengths) to reduce the number of longitudinal mode of the output laser, and its center wavelength of reflection determines the center wavelength of the output beam. Laser diode pump source 101 is determined according to the absorption spectral line of active optical fiber 103 doped with rare earth elements. The parameters of the wavelength division multiplexer 102 and the fiber Bragg grating 104 according to the present invention should be selected to match with the pump wavelength, the laser output beam wavelength, and the parameters of the active optical fiber, the specific parameters are shown in table 1.

TABLE 1 the parameters of the short cavity fiber laser according to the present invention

| Doping element | Peak absorption | Cutoff wavelength | Cladding core diameter | Output laser wavelength | WDM wavelength | FLM wavelength |
|---|---|---|---|---|---|---|
| erbium (Er) | 30 dB/mg @ 1530 nm<br>80 dB/mg @ 1530 nm | 800-980 nm | Single mode 125 μm | 1530 nm-1560 nm | 976/1550 nm | 1550 nm |
| ytterbium (Yb) | 280 ± 50 dB/m @ 920 nm<br>0.6 ± 0.2 dB/m @ 920 nm<br>1.8 ± 0.4 dB/m @ 920 nm | 1010 ± 70 nm | | 1060 nm-1090 nm | 915/1064 nm | 1064 nm |
| Erbium ytterbium codoping | 0.75 ± 0.15 dB/m @ 915 nm<br>40 ± 10 dB/m @ 1535 nm | 1440 ± 80 nm | | 1530 nm-1560 nm | 976/1550 nm | 1550 nm |

According to the present invention, the core diameter of the fiber is determined by the active optical fiber used in the system, cladding core diameter preferably is 125 microns, the core diameter of the optical fiber may be 4 microns, 8 microns or 10 microns, preferably 10/125 microns. The core diameters of the FLM, WDM, LD pigtail fiber should be chose according to the selected core diameter. The pump wavelength of the Erbium-doped fiber used in this system should be 980 nm and 1480 nm, the pump wavelength of the ytterbium doped fiber should be 976 nm and 915 nm, and the pump wavelength of the erbium ytterbium doped fiber should be 976 nm. The parameters of the FLM, WDM should be determined according to the parameters of the wavelength and the core diameter. The laser wavelength outgoing finally is determined by the wavelength of reflection of the fiber Bragg grating in the gain range of the active optical fiber (such as 1530-1560 nm). The typical output beam wavelength of the ytterbium doped fiber is 1535 nm, the typical output beam wavelength of the erbium-doped fiber is 1064 nm, and the typical output beam wavelength of erbium ytterbium doped fiber is 1550 nm.

For example, in this embodiment, when an erbium-doped fiber with a core diameter of 10/125 microns is used as the gain medium, LD pigtail fiber, WDM and FLM will be selected to have the same type core diameters. The output beam wavelength of LD is 976 nm, the operating wavelength of WDM is 976/1550 nm, the operating wavelength of FLM is 1550 nm, the range of FBG is 1530 nm to 1560 nm, a laser output can obtained within this range. If in this embodiment, an ytterbium-doped fiber with a core diameter of 10/125 microns is used as the gain medium, LD fiber, WDM and FLM should be selected to have the core diameter of the same type. LD has a 915 nm single mode output, the operating wavelength of WDM is 915/1064 nm, the operating wavelength of FLM is 1064 nm, FBG is selected near 1064 nm, a laser output can be obtained in the range. The DFB fiber laser is formed by the fiber Bragg grating 104 directly writing on the active fiber 103, while the wavelength of the laser output is kept to be the same with the characteristics lines of the gas absorption are the same.

The laser outputted from the fiber laser according to the present invention is coupled into the optical isolator 105 by the wavelength division multiplexer 102. The optical isolator 105 is used to prevent the reverse optical transmission in the optical fiber from affecting the output light of the gas detection system 100. The operating wavelength and the isolation degree of the optical isolator 105 are chosen based on the parameters of the first and the second emission wavelength. According to a preferable embodiment of the present invention, the operating wavelength of the optical isolator 105 is 1550 nm, the isolation degree of 40 db. The laser after being isolated By optical isolator 105 pass through the coupler 106 with a pigtail fiber of 1×3 and is divided according to a certain power allocation ratio into three beams of light, a reference beam, a detecting beam and a intensity measuring beam. According to a preferable embodiment of the present invention, the coupler 106 has an operating wavelength of 1550 nm, a bandwidth of 40 nm, the ratio for dividing the beam can be chosen according to the situation. As it is required that the beams passing through the reference chamber 107 and the detect chamber 108 are consistent with each other, the light power of the beams passing through the two air chamber are consistent with each other. According to the present invention, preferably the power allocation proportion of the output laser is trisection, namely the ratio of the power of the reference beam:detecting beam:intensity detecting beam (i.e., beams A, B and C respectively, shown in the FIG) is: 1:1:1.

Then, two beams of light are coupled into the reference gas chamber 107 and the detecting gas chamber 108 by the spherical lens 107a and 108a respectively, and then coupled out of a spherical lens 107b and 108b. The detecting gas chamber 108 is used to pass the gas to be detected, and the detect chamber 108 includes a gas inlet 108C to introduce the gas to be detected before measuring and a gas outlet 108d to export the gas. In the measurement process, the gas inlet 108C and gas outlet 108d are closed to achieve a static measurement system. A reference gas chamber 107 is used to judge the stability of the output beam of the laser. The gas inputted into the reference chamber 107 is of the same composition as that of the gas to be detected, and of a known concentration, and the reference chamber 107 is will be completely sealed when measuring.

A first photoelectric detector 109, a second photoelectric detector 110 and a third photoelectric detector 111 are used for detecting the intensity signal of the output light beam, wherein the first photoelectric detector 109 is used to detect the light intensity signal of the laser outputted from the fiber laser after transmitting through a reference gas chamber 107, as a reference signal, namely the first light intensity signal. The second photoelectric detector 110 is used to detect the light intensity signal of the laser outputted from the fiber laser after transmitting through a detecting gas chamber 108, as a light intensity signal, namely the second light intensity signal. The third photoelectric detector 111 is used for detect the light intensity signal of the laser outputted from the fiber laser, namely the third light intensity signal. The third light intensity signal can be used to judge if the laser itself is operating normally, and whether the wavelength of the output beam is consistent with the absorption spectral line of the gas. The intensity of the output light beam can be measured by a power meter or spectrometer. These three light intensity signals are inputted into the feedback control unit 112 for subsequent control operations. Preferably, the photoelectric detector may be made of a photoelectric diode, the operating wavelength range of the photoelectric detector should cover the wavelength range of the output beam of the fiber laser. According to a preferably example of the invention, the operating wavelength of the photoelectric detector is 800-1700 nm, its bandwidth is 1.2 GHz, and its rise time is less than 1.0 ns.

The feedback control unit 112 is used to receive the light intensity signals outputted from the first, the second, and the third photodetectors 109, 110 and 111, and then the light intensity signals are compared and calculated to output the feedback control signal to the laser control unit 113, to implement feedback control. The feedback control unit 112 can be implemented by the single chip microcomputer, integrated circuits, application specific integrated circuit, or computer, its control method will be described in detail below.

The laser control unit 113 preferably can be made of materials such as PZT piezoelectric ceramic or TE temperature control unit etc that can convert electrical signals into physical deformation, that is used to change the cavity length of the laser resonator cavity by material deformation controlled under the feedback signal outputted from the feedback control unit 112, to precisely control the laser output beam wavelength. According to an implementation example of the present invention, the laser control unit 113 can be made by a sheet or plate attached on the fiber Bragg grating 104. When the feedback control unit 112 issues a control signal, the material physical properties of the laser control unit 113 can be changed to change the cavity length of the laser cavity. For example, when the laser control unit 113 is made of piezoelectric ceramic, the feedback control signal makes the laser control unit 113 deform, thus the fiber Bragg grating 104 attached thereto deforms, the length of the laser cavity is changed, the wavelength of the output laser is changed, so that the output beam wavelength drifts.

Figure 2:
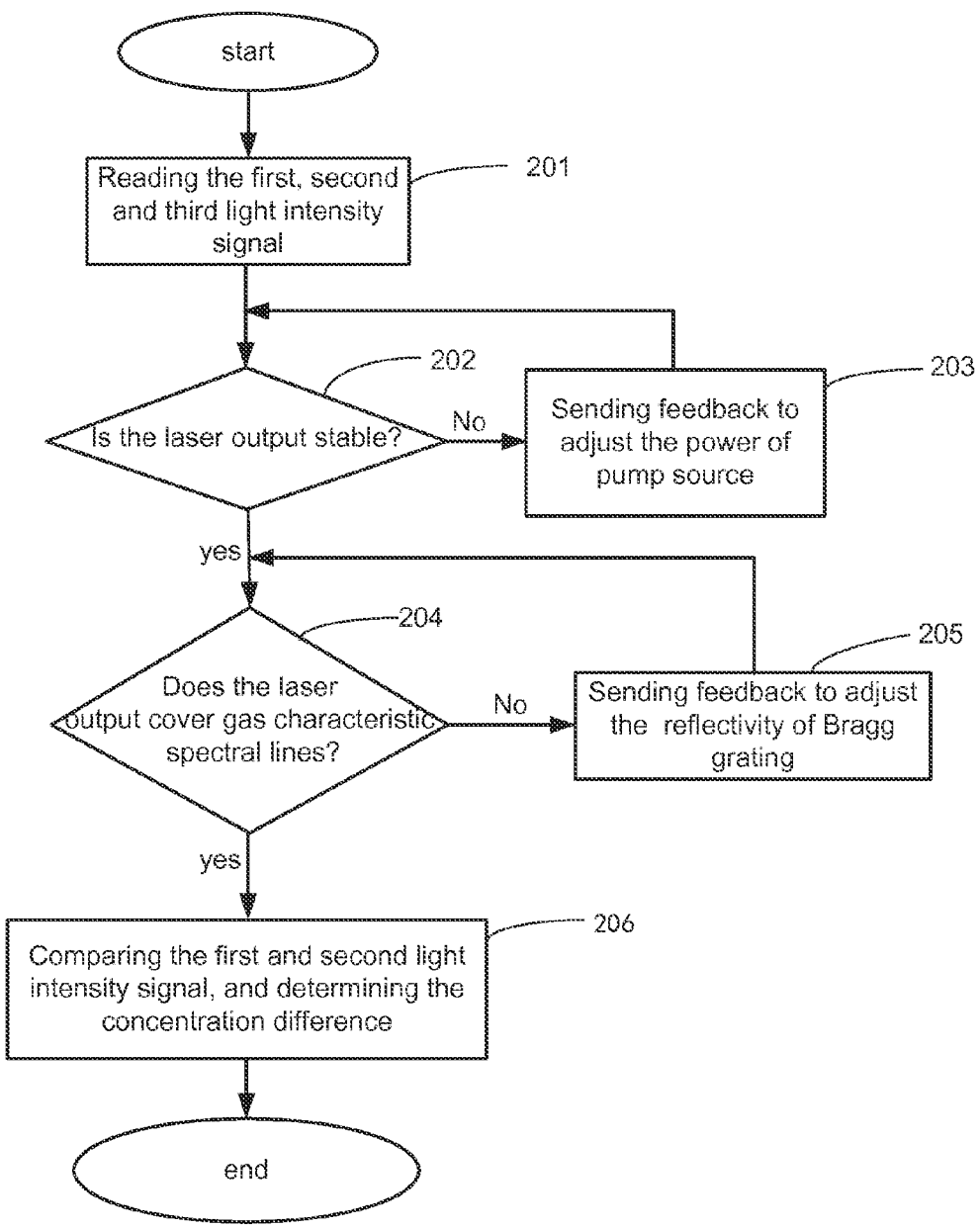
FIG. 2 schematically shows a flow chart of the feedback control method of the feedback control unit according to the present invention.

FIG. 2 shows a flow chart of the feedback control method of the feedback control unit 112 according to the present invention.

At step 201, the first light intensity signal outputted from the first photoelectric detector 109, the second light intensity signal outputted from the second photodetector 110 and the third light intensity signal outputted from the third photoelectric detector 111 are read. The first light intensity signal indicates the light intensity signal after the light outputted from the optical fiber laser transmits through the reference gas chamber 107, as the reference signal, the second light intensity signal indicates the light intensity signal after the light outputted from the optical fiber laser transmits through the detecting gas chamber 108 filled with the gas to be detected, and the third light intensity signal indicates the light intensity signal outputted from the fiber laser itself.

In order to get accurate measurement results, stable and accurate first and second light intensity signals are needed. Therefore, firstly, at step 202, it is judged whether the output of the fiber laser is stable. The stable laser signals generally are shown as signals outputted with intensity in step form. When the system begins to operate, the pump source usually is adjusted to a level of small power output so as to protect the system. With the output power of the pump sources increases and gradually reaches the operating threshold of the laser, a stable laser output is obtained. When at step 202 it is determined that the laser output is not stable, then go to step 203, the first feedback control signal is output by the feedback control unit 112 to adjust the power output of the pump sources, such as to adjust to gradually increase the output power of pump sources. Repeat steps 202 until the laser output achieve stability, i.e., to obtain output signals with intensity in step form as required.

Figure 3:
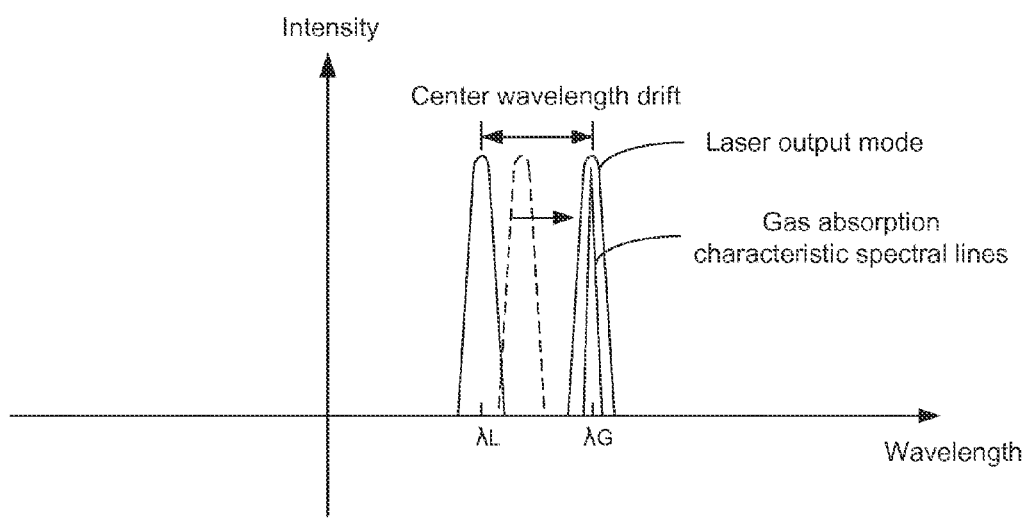
FIG. 3 schematically shows the feedback principle of feedback regulating the drift of the laser output beam wavelength according to the present invention.

Then at step 204, it is determined whether the wavelength range of the signal model outputted from the fiber laser covers the characteristic spectral line of the gas to be detected. FIG. 3 shows the principle of feedback regulating the drift of the output wavelength of the laser beam according to the present invention. As shown in FIG. 3, the center wavelength of the gas absorption spectral lines $l_G$, the center wavelength of laser output mode is $l_L$. If it is desired to measuring gas concentration to be detected through absorbing laser by gas, it is needed to adjust the output of laser so that the center wavelength outputted from the laser drifts, until it completely covers the center wavelength of the absorption spectral line of the gas to be detected. Ideally, when $l_G$ and $l_L$ substantially coincidence, the measurement achieves the best effect, namely the output of the laser is completely absorbed by the reference gas and the gas to be detected, the intensity of the laser after passing through the reference chamber and the detecting gas chamber reduces significantly.

It can be determined whether the wavelength range of the signal model outputted from the fiber laser covers the characteristic spectral line of the gas to be detected, by comparing the intensity of the first or the second light intensity signal with that of the third light intensity signal which is not absorbed by the gas. If the wavelength range of the signal model outputted from the fiber laser is coincident basically with the characteristic spectral line of the gas to be detected, the laser is absorbed completely, and the signal intensity of the first or second light intensity signal will be significantly less than the third light intensity signal without being absorbed by gas. If wavelength misalignment leads to the light is not absorbed by gas, the signal intensity of the first or second light intensity signal should be substantially the same as that of the third light intensity signal, and the attenuation of the first or second light intensity signal passing through the air chambers should be negligible. The attenuation degree of the intensity of the laser being absorbed by the gas comparing that of the laser not being absorbed by the gas depends on the different gas concentrations and absorption lines of the gas to be detected.

When it is found that the center of the wavelength of the laser output signal does not coincident with the center wavelength of the characteristics spectral line of the gas to be detected when comparing the signal intensity, go to step 205. The feedback control unit 112 transmits the second feedback control signal to the laser control unit 113 to control the reflectivity of the Bragg grating 104, so that the laser control unit 113 deforms to change the laser resonator cavity length, which precisely control the laser output beam wavelength to drift till it move to be substantially coincident with the center wavelength of the characteristics absorption spectral lines of the gas to be detected. When for example the laser control unit 113 is made of piezoelectric ceramic materials sheet or plate sheet, the laser control unit 113 deforms under the control of the feedback control signal, which makes the fiber Bragg grating 104 attached thereto deforms, thus changing the laser cavity length, changing the wavelength of the laser output which drifts. Then, go to step 206.

At step 206, the signal intensities of the first light intensity signal and a second light intensity signal are compared, and the difference between the two intensities value indicates the comparing result of the concentration of the gas to be detected and the reference gas. For example, if the intensity value of the second light intensity signal is greater than the intensity value of the first light intensity signal, the gas concentration of the detecting gas chamber 108 is greater than that in the reference gas chamber 107. Preferably, the comparison results can be outputted to an alarm device, which trigger the alarm signal when the alarm threshold is reached.

The gas detection system according to the present invention can be constructed to select different components parameters based on the type and the concentration of the gas to be detected. For example, the gas detection system of the present invention is applied to detect the methane content in an industrial environment. In the industrial environment, it is required that the content of methane gas is not higher than 4%, otherwise it will explode. When the gas detection system according to the present invention is used, the reference gas chamber is filled with the reference gas with a methane content of 4%, and the components of the laser is chosen to make the wavelength range of the laser output covers the center wavelength of the absorption characteristic spectral line of methane. Then, the gas detection system is placed in the environment to be detected, the inlet of the detecting gas chamber is open so that a certain amount of gas sample to be detected is introduced into the chamber, and then the gas inlet and gas outlet of the detecting gas chamber is closed. Next, the laser of the gas detection system is open, so that laser outputted from the laser pass through the reference gas chamber and the detecting gas chamber respectively. The output of the laser is measured. Next, by adjusting the power of the pump sources to be used and the reflectivity of the fiber Bragg grating, a stable laser output is achieved to cover the absorption spectrum line of methane gas. By comparing light intensities of the laser passing through the reference gas chamber and the detecting gas chamber, it can be determined whether methane gas concentration in this industrial environment exceeds the threshold value of methane content, and the alarm system is triggered immediately when it exceeds the threshold value.

The gas detection system according to the present invention can take advantages of the unique superiority of the compact structure and narrow linewidth of the laser output of the fiber laser, and achieve a gas detection method with high sensitive and high precision by feedback controlling. The method and system are not limited to apply to high sensitivity detection of gas content, but also easily apply to the detection with high sensitivity and material analysis of other materials.

Combined with the disclosed description and practice of the present invention, it is easy for those skilled in the art to contemplate and understand other embodiments of the invention. The description and embodiments are merely exemplary, and the scope and spirit of the invention will be limited by the claims.

What is claimed is:

1. A fiber laser gas detection system using active feedback compensation by a reference cavity, said system comprising:
   an optical fiber laser consists of a laser diode pump source, a wavelength division multiplexer, an active optical fiber and a fiber Bragg grating connected successively;
   an optical isolator coupled with said wavelength division multiplexer for blocking a reverse light transmission in said active fiber;
   a coupler connected with said optical isolator for dividing the laser light after being isolated by the optical isolator into a reference beam, a detecting beam and an intensity measuring beam according a certain ratio of power;
   a reference gas chamber, which is introduced with a reference gas of the same composition as that of the gas to be detected and of a known concentration, and receives the reference beam allocated from the coupler and makes the beam pass through the reference gas;
   a detection gas chamber, which is introduced with the gas to be detected, and receives the detecting beam allocated from the coupler and makes the beam pass through the gas to be detected;
   a first photodetector connected to said reference gas chamber for receiving the reference beam passing through the reference gas chamber to generate a first light intensity signal;

a second photodetector connected to said detection gas chamber for receiving the detecting light beam passing through the detection gas chamber to generate a second light intensity signal;

a third photodetector connected to said coupler for receiving said intensity measuring beam to generate a third light intensity signal;

a feedback control unit for receiving and comparing said first, second and third light intensity signals, and converting the comparison result into a feedback signal to adjust said pump source and said fiber Bragg grating.

2. The gas detection system as claimed in claim 1, wherein the power ratio of the reference beam, the detecting beam and the intensity measuring beam is 1:1:1.

3. The gas detection system as claimed in claim 1, wherein the feedback control method of the feedback control unit comprising the steps of:
 a) determining whether the output of the fiber laser is stable, if it is not stable, outputting a first feedback control signal to adjust the power output of the pump source until it is stable;
 b) determining whether the wavelength range of the signal mode outputted from the fiber laser covers the characteristics spectral lines of the gas to be detected, if it does not cover, then outputting a second feedback control signal to adjust the reflectivity of fiber Bragg grating until it covers;
 c) comparing the signal intensities of the first and second light intensity signals to obtain the result of comparing the concentrations of the gas to be detected and the reference gas.

4. The gas detection system as claimed in claim 3, wherein said step b) is achieved by comparing if the signal intensity values of said first or second light intensity is substantially smaller than that of the third light intensity signal to determine whether it covers.

5. The gas detection system as claimed in claim 3, further comprising a laser control unit attached to the fiber Bragg grating, and the deformation of the laser control unit is controlled by said second feedback control signal so as to change the laser resonator cavity length.

6. The gas detection system as claimed in claim 5, wherein the laser control unit is made of PZT piezoelectric ceramic or TE temperature control unit.

7. The gas detection system as claimed in claim 5, wherein the gas detection system is a wavelength division multiplexed device of 1×2.

8. The gas detection system as claimed in claim 1, further comprising a spherical lens for respectively coupling the reference beam and the detecting beam into the reference gas chamber and the detection gas chamber so as to emit therefrom.

9. The gas detection system as claimed in claim 1, wherein the active fiber is an ytterbium-doped fiber, or erbium-doped fiber or erbium ytterbium co-doped fiber.

10. The gas detection system as claimed in claim 1, wherein said detection gas chamber comprises a gas inlet to introduce the gas to be detected before detection and a gas outlet to exhaust the gas.

\* \* \* \* \*